US010064700B2

(12) United States Patent
Fudim

(10) Patent No.: US 10,064,700 B2
(45) Date of Patent: Sep. 4, 2018

(54) SURGICAL GUIDE KIT APPARATUS AND METHOD

(71) Applicant: Zvi Fudim, Dollard-des Ormeaux (CA)

(72) Inventor: Zvi Fudim, Dollard-des Ormeaux (CA)

(*) Notice: Subject to any disclaimer, the term of this patent is extended or adjusted under 35 U.S.C. 154(b) by 0 days.

(21) Appl. No.: 13/766,814

(22) Filed: Feb. 14, 2013

(65) Prior Publication Data

US 2014/0227656 A1    Aug. 14, 2014

(51) Int. Cl.
*A61C 1/08* (2006.01)
*A61C 13/00* (2006.01)
*A61C 13/34* (2006.01)

(52) U.S. Cl.
CPC .......... *A61C 1/082* (2013.01); *A61C 13/0004* (2013.01); *A61C 13/34* (2013.01)

(58) Field of Classification Search
CPC .... A61C 1/084; A61C 9/002; G06F 17/30873
USPC ................................................ 433/24, 72-75
See application file for complete search history.

(56) References Cited

U.S. PATENT DOCUMENTS

| | | | | |
|---|---|---|---|---|
| 4,870,290 A * | 9/1989 | Deck | 250/559.31 |
| 5,084,980 A * | 2/1992 | Skopec et al. | 33/286 |
| 5,415,546 A * | 5/1995 | Cox, Sr. | 433/213 |
| 5,527,182 A * | 6/1996 | Willoughby | 433/172 |
| 5,556,278 A * | 9/1996 | Meitner | 433/75 |
| 5,636,986 A * | 6/1997 | Pezeshkian | 433/76 |
| 5,725,376 A * | 3/1998 | Poirier | 433/172 |
| 5,743,916 A * | 4/1998 | Greenberg et al. | 606/102 |
| 5,778,043 A * | 7/1998 | Cosman | 378/65 |
| 5,888,034 A * | 3/1999 | Greenberg | 408/115 R |
| 5,927,982 A * | 7/1999 | Kruger | 433/215 |
| 5,947,981 A * | 9/1999 | Cosman | 606/130 |
| 6,087,618 A * | 7/2000 | Wiener-Avnear et al. | 219/121.6 |
| 6,143,003 A * | 11/2000 | Cosman | 606/130 |
| 6,283,753 B1 * | 9/2001 | Willoughby | 433/172 |
| 6,382,975 B1 * | 5/2002 | Poirier | 433/173 |
| 6,606,403 B2 * | 8/2003 | Freifeld | 382/152 |
| 6,634,883 B2 * | 10/2003 | Ranalli | 433/50 |
| 6,814,575 B2 * | 11/2004 | Poirier | 433/75 |
| 7,097,451 B2 * | 8/2006 | Tang | 433/76 |
| 7,204,032 B2 * | 4/2007 | Matsuda et al. | 33/503 |

(Continued)

FOREIGN PATENT DOCUMENTS

CN        202741783 U  *  2/2013  ............. B23B 39/00

OTHER PUBLICATIONS

Block et al., The Navigator System for Minimally Invasive Computed Tomography Guided Surgery, Biomet 3i, vol. 3, Issue 2, Fall 2007, pp. 6 and 7, http://biomet3i.com/Resource%20Center/EYE %20ON%203i%20NEWSLETTER%20ARCHIVE/2007/Fall %202007_en.pdf.*

*Primary Examiner* — Heidi M Eide
*Assistant Examiner* — Mirayda A Aponte
(74) *Attorney, Agent, or Firm* — Gonzalo Lavin

(57) ABSTRACT

A method for fabricating a dental surgical guide. The method includes the steps of producing a dental cast dental cast from an edentulous patient jaw; drilling the dental cast model for inserting a radiopaque rod therein; molding a base plate thereon to produce a radiopaque marker appliance; scanning the resulting appliance in a patient's mouth using computed tomography; calculating angles from the computed tomography for adjusting protractors of a dental model laser aligner; and molding a base-plate that incorporates a telescopic drilling tube that results into the dental surgical guide.

1 Claim, 22 Drawing Sheets

(56) References Cited

U.S. PATENT DOCUMENTS

| | | | |
|---|---|---|---|
| 7,698,014 B2* | 4/2010 | Dunne et al. | 700/118 |
| 7,835,811 B2* | 11/2010 | Schmitt | 700/98 |
| 7,950,131 B2* | 5/2011 | Hilliard | 29/564 |
| 8,002,465 B2* | 8/2011 | Ahn | 378/205 |
| 8,011,927 B2* | 9/2011 | Berckmans et al. | 433/215 |
| 8,021,153 B2* | 9/2011 | Poirier | 433/173 |
| 8,170,327 B2* | 5/2012 | Glor et al. | 382/154 |
| 8,221,121 B2* | 7/2012 | Berckmans et al. | 433/215 |
| 8,246,352 B2* | 8/2012 | Takebayashi | 433/75 |
| 8,359,114 B2* | 1/2013 | Steingart et al. | 700/98 |
| 8,425,227 B2* | 4/2013 | Marotta | 433/72 |
| 8,473,305 B2* | 6/2013 | Belcher et al. | 705/2 |
| 8,582,870 B2* | 11/2013 | Glor et al. | 382/154 |
| 2002/0016600 A1* | 2/2002 | Cosman | 606/130 |
| 2004/0120781 A1* | 6/2004 | Luca et al. | 409/84 |
| 2004/0120844 A1* | 6/2004 | Tribelsky et al. | 422/2 |
| 2005/0259863 A1* | 11/2005 | Freifeld | 382/152 |
| 2007/0196782 A1* | 8/2007 | Noguchi | 433/56 |
| 2008/0261165 A1* | 10/2008 | Steingart et al. | 433/24 |
| 2009/0068617 A1* | 3/2009 | Lauren | 433/213 |
| 2009/0087276 A1* | 4/2009 | Rose | 409/79 |
| 2009/0092948 A1* | 4/2009 | Gantes | 433/215 |
| 2009/0130630 A1* | 5/2009 | Suttin et al. | 433/174 |
| 2009/0197219 A1* | 8/2009 | Rizzo | 433/173 |
| 2010/0124731 A1* | 5/2010 | Groscurth et al. | 433/213 |
| 2010/0151417 A1* | 6/2010 | Nilsson et al. | 433/167 |
| 2010/0173260 A1* | 7/2010 | Sogo et al. | 433/75 |
| 2010/0233647 A1* | 9/2010 | Yang | 433/66 |
| 2010/0291508 A1* | 11/2010 | Jensen | 433/174 |
| 2010/0311028 A1* | 12/2010 | Bell et al. | 434/263 |
| 2011/0045431 A1* | 2/2011 | Groscurth et al. | 433/74 |
| 2011/0060343 A1* | 3/2011 | Scortecci | 606/96 |
| 2011/0104632 A1* | 5/2011 | Colby | 433/29 |
| 2011/0117516 A1* | 5/2011 | Takebayashi | 433/29 |
| 2011/0129792 A1* | 6/2011 | Berckmans et al. | 433/72 |
| 2011/0136077 A1* | 6/2011 | De Moyer | 433/173 |
| 2011/0200961 A1* | 8/2011 | Colby | 433/29 |
| 2011/0245951 A1* | 10/2011 | Gantes | 700/98 |
| 2011/0262885 A1* | 10/2011 | Weber et al. | 433/202.1 |
| 2011/0280674 A1* | 11/2011 | Palti et al. | 408/1 R |
| 2011/0306009 A1* | 12/2011 | Suttin et al. | 433/75 |
| 2011/0318703 A1* | 12/2011 | Moriyama et al. | 433/69 |
| 2012/0028213 A1* | 2/2012 | Meitner | 433/74 |
| 2012/0116203 A1* | 5/2012 | Vancraen et al. | 600/407 |
| 2012/0283866 A1* | 11/2012 | Berckmans et al. | 700/119 |
| 2012/0316486 A1* | 12/2012 | Cheung et al. | 602/48 |
| 2012/0323546 A1* | 12/2012 | Berckmans et al. | 703/11 |
| 2013/0017507 A1* | 1/2013 | Moffson et al. | 433/27 |
| 2013/0023888 A1* | 1/2013 | Choi et al. | 606/96 |
| 2013/0280673 A1* | 10/2013 | Maksim | 433/75 |
| 2013/0337400 A1* | 12/2013 | Yi et al. | 433/25 |

* cited by examiner

SURGICAL GUIDE KIT APPARATUS AND METHOD

CROSS-REFERENCE TO RELATED APPLICATION

This application claims the benefit, under 35 U.S.C. § 119(e), of U.S. Provisional Application No. 61/598,616, filed Feb. 14, 2012. The above document is incorporated herein in its entirety by reference.

FIELD OF THE INVENTION

This invention relates generally to artificial teeth implantation in patients' jaw bone.

BACKGROUND OF THE INVENTION

Dental implantation is a surgical procedure whereby a root-form endosseous part usually made of titanium is introduced into the edentulous area of the patient' jawbone. The main purpose of this dental implantation is to restore the patient's mastication ability and to improve his or her appearance, due to absence of natural teeth. The root-form endosseous part, when integrated in the recipient jawbone, is called a dental implant.

The basic procedure of implant introduction consists of cutting into the bone using precision drills that have highly regulated speeds. This results in a cylindrical osteotomy that corresponds to the length and the diameter of the implant. Such implants are usually equipped with retention and thread, to insure initial stability in the bone.

Careful and detailed planning before surgery is required for the best outcome. Important structures must be identified such as the inferior alveolar nerve and the maxillary sinus. Identifying the shape and dimensions of the bone is also important. This planning usually involves a series of X-ray, computed tomography (CT) and study impressions.

Study of patients' X-rays and models reveals that resorption of the alveolar ridge often occurs as a consequence of teeth loss. Loss of teeth alters the form of the alveolar bone in 91% of cases.

The preparation of the osteotomies requires great precaution due to the extensive residual ridge resorption. Many sites become much closer to the osteotomy, such as the inferior alveolar nerve and the mental foramen within the mandible, as well as other important anatomic elements such as adjacent teeth, the buccal plate and the maxillary sinus.

A surgical guide may sometimes be used to facilitate the preparation of the osteotomy.

The surgical guide is an acrylic baseplate that can be fitted over teeth, the bone surface, or the mucosa (if all teeth are missing). It is fitted with pre-drilled straight lumens, which are dependent on the position and the angle of the implants to be placed. The surgical template can be produced from stereo lithography, as when the case is planned on computer following a CT scan. (U.S. Pat. No. 6,382,975).

RELATED ART

It is known in dental surgery is to make a cast impression of a patient's mandible and/or maxilla in order to design, or select, the appropriate prosthetic device. A diagnostic tooth set-up or wax-up is used on a cast to determine the most desirable tooth position in the final restoration.

To locate and create an osteotomy for a dental implant, still the most commonly used method is simply to survey the area visually and drill according to this visual inspection.

If the patient is completely edentulous, an acrylic tooth set-up may be used to locate the most desirable tooth position for the final restoration.

For an acrylic tooth set-up, the dental technician drills through the tooth set-up to make a mark on the patient's dental cast model. The acrylic set-up is then removed, and the cavity is used for the orientation of the implant osteotomy.

However, this requires the teeth to be set-up or wax up, which is time-consuming and requires dental technician skills. The dentist spends a great deal of time communicating with the technician to choose the correct angle for the osteotomy, which does not usually corresponds with the angle of the acrylic set-up teeth. U.S. Pat. No. 5,556,278 and US20120028213A1.

The wax-up and set-up procedures act to partition the edentulous space. However, this is not on the level of the residual ridge surface, but on the level of the occlusal plane. The result of these procedures is therefore unpredictable since the occlusal plane level is far from the residual ridge surface. The wax-up and the set-up have a great diagnostic value but they cannot replace the process of partitioning the residual ridge surface.

It is difficult to visualize the radiopaque sleeves, which are short and wide; this makes it very difficult to determine the long axis. U.S. Pat. No. 5,556,278 and US20120028213A1.

The round cross-section shape-guide post cannot be immobilized in the stone cast due to its material properties, which causes errors in the orientation of the osteotomy. U.S. Pat. No. 5,556,278 and US20120028213A1.

There is a large distance between the sleeve and the jawbone, and the drill bit is not long enough to perform a full-depth osteotomy. U.S. Pat. No. 5,556,278 and US20120028213A1.

The sleeve has limited access in the posterior areas due to its large length, especially when the mouth opening is small. U.S. Pat. No. 5,556,278 and US20120028213A1.

Therefore, the present invention provides improvements in producing the surgical guide in-office by the dentists, or at conventionally-equipped dental labs.

It is further an object of the present invention to provide a kit of the materials, supplies and instructions in order to produce surgical guides by the provided methods.

The improvements in which the present invention makes will become increasingly apparent in the following description.

SUMMARY OF THE INVENTION

The present invention is an improvement of the inventions patented in U.S. Pat. No. 5,556,278 and US20120028213A1, and it can produce surgical guides for Intraosseous dental implants more accurately and more quickly.

The present invention comprises of a method and a kit for the instant in-office fabrication of a surgical guide as disclosed. The kit includes: a dental model laser aligner tool for aligning a dental cast model into direction of dental implant osteotomy, a Program for dental implant osteotomy complementary angles calculation, self-adhesive partitioning dental stickers for partitioning an edentulous space of the dental cast model, telescopic composed drilling tubes for dental implant osteotomy and radiopaque rods for dental implant osteotomy CT visualization.

The method comprises of:

a) producing a dental cast model of the edentulous patient's jaw;
b) partitioning the edentulous space with the aid of the self-adhesive partitioning dental stickers;
c) drilling a Straight Cavity in the dental cast model in the spot designated by the self-adhesive partitioning dental stickers;
d) inserting a radiopaque rod into the drilled straight cavity;
e) molding a base plate incorporating the radiopaque rod;
f) removing the base plate with the radiopaque rod from the dental cast model;
g) trimming the radiopaque rod at the mucosa level resulting a radiopaque marker appliance for a radiographic visualization.
h) Further, the process comprises of constructing of an angle on the sagittal view and constructing of an angle on the panoramic view of the CT. The vertex of each angle should begin at the mucosal end of the radiographic depiction of the radiopaque rod. The occlusal side of each angle crosses along the radiopaque rod, and the apical side of each angle is oriented in the middle of the osteotomy site.
i) Further, the angles are analyzed to determine the direction of the tipping of the occlusal side of the angle towards the direction of the osteotomy.
j) Then, in the dental model laser aligner, the complimentary sagittal angle is set in the sagittal rotating head, and the complementary panoramic angle is set in the panoramic rotating head.
k) Then, the removable linear reflector is inserted in the drilled straight cavity with the horizontal extension oriented towards buccal;
l) Then, the model is aligned with that aid of the dental model holder for dental implant models until both lasers are intersected onto the removable linear reflector including the buccal surface of the horizontal extension.
m) Then, at the same time as the removable linear reflector is removed from the drilled straight cavity, a new radiopaque rod is attached to the parallel arm of the dental model laser aligner and moved over the straight drilled cavity opening on the dental cast model.
n) Then, gluing the radiopaque rod to the dental cast model;
o) inserting a telescopic composed drilling tube over the radiopaque rod.
p) The final step is to mold a base plate incorporating the telescopic composed drilling tube;
q) removing the base plate with the telescopic composed drilling tube from the dental cast model.

The present invention provides a kit which comprises all the necessary materials and supplies in a plastic carrying case. The kit can be easily moved between locations as needed. In the kit are also included all necessary educational materials in written, video, and CD formats, as well as contact information for reordering and technical support information.

The self-adhesive partitioning dental stickers, which are made of a soft plastic material and have adhesive on one of their surfaces, are applied onto the residual ridge.

The shape and size of each sticker should match the occlusal projection of the corresponding prosthetic tooth.

The self-adhesive partitioning dental stickers are applied to partition the residual ridge, and there are equal to, or smaller than, the diameter of the residual ridge length.

The reason for the use of the self-adhesive partitioning dental stickers is to decrease the chance of mistakes, by decreasing the range of error distribution.

$$L\alpha > (L-LS)\alpha$$

L=the total residual ridge length, mesial-distal
α=continuous probability distribution
LS=the total length of stickers, mesial-distal The self-adhesive partitioning dental stickers are organized on folia so that they can be picked up easily with dental tweezers.

The self-adhesive partitioning dental stickers are organized to be easily identifiable by tooth number.

The self-adhesive partitioning dental stickers have a mark in their center through which one can mark or drill.

The self-adhesive partitioning dental stickers comprising alignment marks in their buccal areas to facilitate the correct orientation of the sticker on the residual ridge.

The kit also comprises radiopaque rods. The radiopaque rods have a polygonal cross-section that provides a tight fit into the drilled straight cavity in the dental cast model.

The kit also comprises a dental model laser aligner which comprises of: a base, one rotating head for a sagittal view, and another rotating head for a panoramic view, one dental model holder for dental implant models and one parallel arm.

The kit also comprises the telescopic composed drilling tubes. These telescopic composed drilling tubes are essentially exterior plastic tubes comprising an interior stainless steel tube. The inner diameter of the exterior tube is similar to the outer diameter of the interior tube.

CAD/CAMs of the surgical guide can be produced. This is because the present invention allows for 3D scanning of patients models with the aid of a computer program. This scanning enables computation of a corrected virtual osteotomy axis, which uses sagittal and panoramic angles and which is similar to the intersection of the two laser beams of the dental model laser aligner. The present invention applies an angle correction for each osteotomy trajectory and this is unlike the previous art (US00/5725376A), where a model is linked to one reference point and this point is considered as 0,0,0,x,y,z.

FIGURES

FIG. 1 Self-adhesive partitioning dental stickers—top view
FIG. 2 Self-adhesive partitioning dental stickers—perspective view
FIG. 3 Edentulous space partitioning
FIG. 4 Model drilling
FIG. 5 Edentulous drilled model
FIG. 6 Edentulous drilled model section AA view
FIG. 7 Radiopaque rod insertion
FIG. 8 Radiopaque marker appliance baseplate
FIG. 9 Radiopaque marker appliance
FIG. 10 Sagittal view CT of the present invention
FIG. 11 Panoramic view CT of the present invention
FIG. 12 Complementary angle calculating program (a screen snapshot)
FIG. 13 Dental model laser aligner
FIG. 14 Gluing the radiopaque rod
FIG. 15 Telescopic composed drilling tube for drilling implant osteotomy
FIG. 16 Telescopic composed drilling tube insertion
FIG. 17 surgical guide baseplate molding
FIG. 18 surgical guide mucosal view
FIG. 19 surgical guide occlusal view
FIG. 20 3D digital version of the present invention (a screen snapshot)

FIG. 21 Top view of a radiopaque rod inserted into a telescopic composed drilling tube FIG. 22 Alignment on the dental model laser aligner FIG. 23 Removable linear reflector FIG. 24 Removable linear reflector inserted in the straight cavity FIG. 25 Axes of the rotation of the rotating heads FIG. 26 surgical guide workflow

DETAILED DESCRIPTION OF THE INVENTION

It is therefore an object of the invention to provide a method to transfer the angles of the planned osteotomy from the computed tomography (CT) or cone beam computed tomography (CB), to the model in order to fabricate a surgical template.

The method comprises of:

a) Producing of a dental cast model 300 (FIG. 3) from an edentulous patients jaw;

b) Tracing a line 301 along the center of the edentulous ridge following application of self-adhesive partitioning dental stickers 104 (FIG. 3) on the line 301;

c) Using a simple drill press 400 (FIG. 4), equipped with an appropriate drill bit 402, to drill the model 300 through the designated hole 105 of the self-adhesive partitioning dental stickers 104 approximately in the perpendicular direction 500 (FIG. 5) to the table plan 403 producing a straight cavity 600 (FIG. 6) with the cavity opening 401;

d) Inserting a radiopaque rod 700 (FIG. 7), which is a disposable plastic stick with a polygonal cross-section, with the size that fits to the straight drilled cavity, whereby vertexes touch the inner surface of the straight drilled cavity 600, in the straight cavity 600 of the dental cast model 300;

e) Molding a base plate 800 (FIG. 8) on the dental cast model 300 incorporating the radiopaque rod 700 resulting a radiopaque marker appliance 900 (FIG. 9);

f) Removing the radiopaque marker appliance 900 from the dental cast model 300;

g) trimming the radiopaque rod 700 at the mucosal level of the radiopaque marker appliance 900;

h) Radiographic visualization CT or CB of the radiopaque marker appliance 900 in a patient's mouth (FIG. 10 and FIG. 11). Then, the process comprises steps of angles construction:

i) Constructing a sagittal angle 1001 on the sagittal view 1000 (FIG. 10) of the CT image with a vertex at the mucosal end 1006 of the radiographic depiction 1002 of the radiopaque rod 700 where the occlusal side 1003 of the angle 1001 is located in the middle of a radiographic depiction 1002 of the radiopaque rod 700 and the apical side 1004 is oriented in the middle of the osteotomy site 1005 which is represented by a virtual implant 1007 located in the body of the jawbone 1008;

j) Analyzing the angle 1001 to determine the direction of the tipping 1012 of the occlusal side of the angle 1001 towards the axis of the osteotomy 1013.

k) Constructing of a panoramic angle 1101 on the panoramic view 1100 of the CT image with vertex at the mucosal end 1106 of the radiographic depiction of the radiopaque rod 1102 of the radiopaque rod 700 where the occlusal side 1103 of the angle 1101 is located in the middle of the radiographic depiction of the radiopaque rod 1102 and the apical side 1104 is oriented in the middle of the osteotomy site 1105 which is represented by a virtual implant 1107 located in the body of the jawbone 1108.

l) Analyzing the angle 1101 to determine the direction of the tipping 1112 of the occlusal side of the angle 1101 towards the axis of the osteotomy 1113.

m) Further steps comprise of: entering into the input part 1203 of the program 1200 (FIG. 12) the following information: a tooth number in the input field 1205, the value of the sagittal angle 1001 in the input filed 1206, the value of the panoramic angle 1101 in the input field 1207;

n) Selecting into the input part 1203 of the program 1200 a proper tipping 1208 of the angle at the occlusal side 1003 from the sagittal view 1000, and selecting a proper tipping 1209 of the angle's side 1103 from the panoramic view 1100;

o) Calculating with the aid of a computer program 1200 the following data into the output part 1204: the value of the first angle, a sagittal complementary angle 1011 (FIG. 10) of the sagittal view 1000, the value of the complementary angle 1111 (FIG. 11) of the panoramic view 1100, and the sense of the rotation 1202 of the first rotating head 1301 and second rotating head 1302, which rotate on the columns 1307 (FIG. 13);

p) Setting the calculated value of the first angle, the sagittal complementary angle 1011, in the first protractor, a sagittal protractor 1313, and the second angle, the panoramic complementary angle 1111, in the second protractor, a panoramic protractor 1314, of the dental model laser aligner 1300;

q) Aligning the model 300 by sliding and articulating the dental model holder for dental implant models 1309 on the platform 1312 until the first linear laser source, a sagittal laser 1303, and the second linear laser source, a panoramic laser 1304, intersect onto the removable linear reflector rod 1305 which is inserted in the drilled straight cavity 600 of the model 300, and oriented with the horizontal extension 2304 towards buccal (FIG. 24). The model 300 is aligned only when the sagittal laser beam 2201 (FIG. 22) is entirely aligned on the first reflecting surface 2302 (FIG. 23) of a removable linear reflector rod 1305 (FIG. 22) and at the same time the panoramic laser beam 2202 (FIG. 22) is entirely aligned on the second reflecting surface 2303 and third reflecting surface 2305 (FIG. 23) of a removable linear reflector rod 1305;

r) Engaging a new radiopaque rod 1400 (FIG. 14) to the chuck 1401 of a parallel arm 1306 (FIG. 13);

s) Removing the removable linear reflector rod 1305 from the drilled straight cavity 600 and positioning the new radiopaque rod 1400, which is attached to the chuck 1401, exactly over the cavity opening 401;

t) Lowering the spindle 1311 until the rod 1400 touches the model 300 (FIG. 14);

u) Gluing the rod 1400 with instant glue 1402 to the model 300 (FIG. 14);

v) Once the glue sets, the spindle 1311 with the chuck 1401 are lifted up having the new radiopaque rod 1400 to stay attached to the model 300 in the right position;

w) Inserting a telescopic composed drilling tube for drilling implant osteotomy 1500 (FIG. 16), which is essentially a stainless steel tube 1501 (FIG. 15) with a lumen 1503 overlapped by an outer plastic tube 1502, over each radiopaque rod 1400;

x) Lowering the outer plastic tube 1502 to the mucosal level 1600 (FIG. 16) of the dental cast model 300;

y) On the dental cast model 300 molding a base-plate 1700 (FIG. 17), which incorporates the telescopic composed drilling tubes 1500;

z) Once the base-plate material has set, the surgical guide 1800 (FIG. 18) can be removed from the dental cast model 300;

aa) Positioning the distal end 1504 the stainless steel tube 1501 (FIG. 15) of the telescopic composed drilling tube 1500 on the jawbone level;

bb) Gluing with aid of instant glue the stainless steel tube 1501 (FIG. 18) to the outer plastic tube 1502 producing a surgical guide 1800 with drilling tubes that have a lumen 1503 for a first pilot surgical drill bit (FIG. 19) to drill the osteotomy.

FIG. 20 In a particular plurality of embodiments, the present invention comprises a 3D digital version 2000 (FIG. 20). In that case, similarly to the previously described method, the real dental cast model 300 is partitioned with an aid of the self-adhesive partitioning dental stickers, following the drilling and insertion of the radiopaque rod. Then, this model is scanned and a 3D virtual/digital image 2300 (FIG. 20) is created. Furthermore, the virtual/digital image 2300, including the virtual radiopaque rod 2002, can be virtually aligned with the vector 2001. The alignment is made with the aid of horizontal lever 2003 and vertical lever 2004. The vector 2001 is calculated from the CT sagittal view 1000 and the panoramic view 1100. Aligning the virtual model 2300 allows a CAD/CAM surgical guide to be produced.

FIG. 1 and FIG. 2 show the layout of the self-adhesive partitioning dental stickers on the base foil 103. The self-adhesive partitioning dental stickers 104 comprises a mark 106 on the buccal side, and a round hole 105 in the center.

Figure 1:
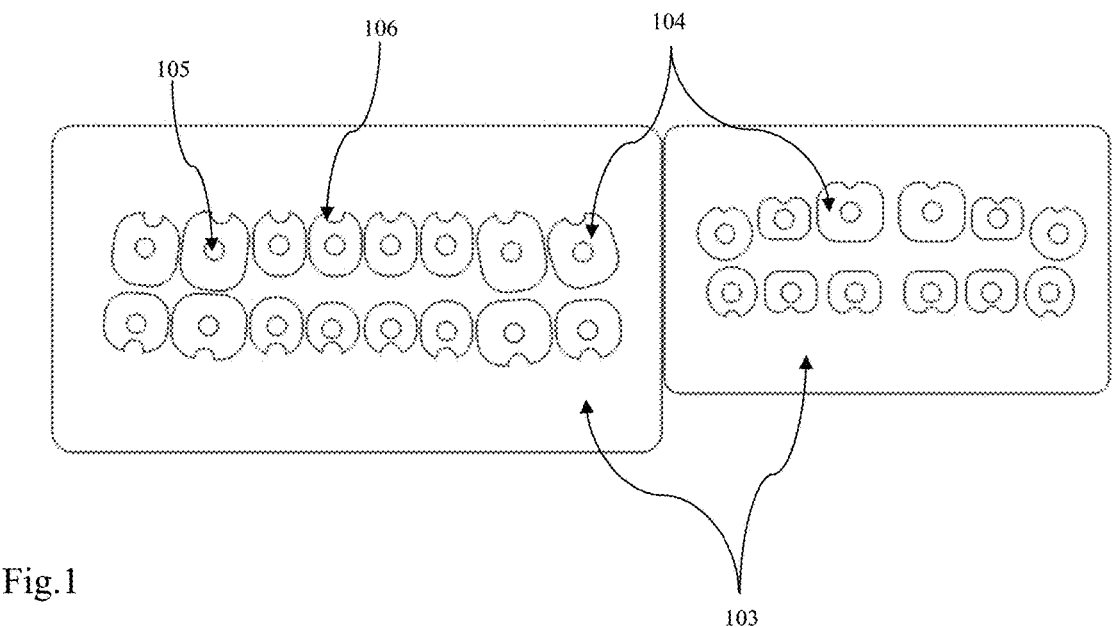
Figure 2:
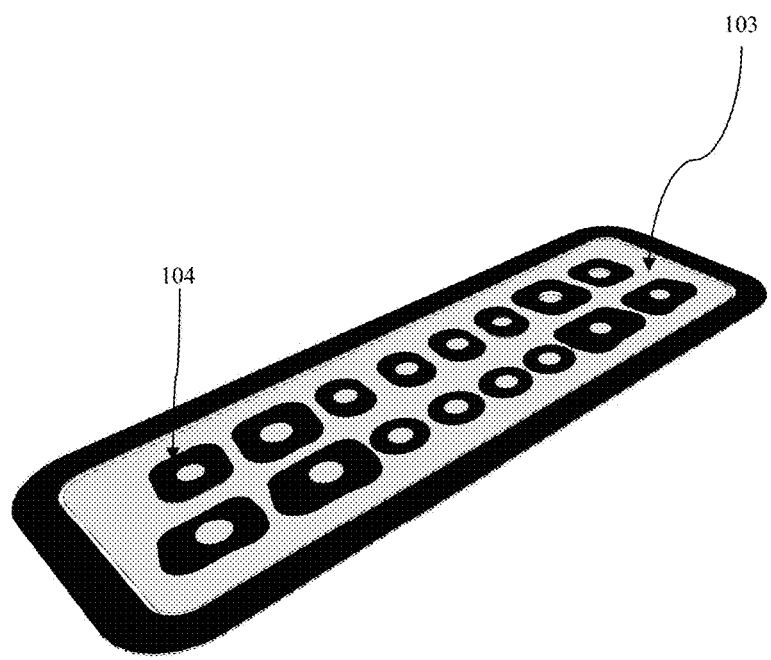
FIG. 2 shows a posterior self-adhesive partitioning dental stickers set, from a perspective view.
Figure 3:
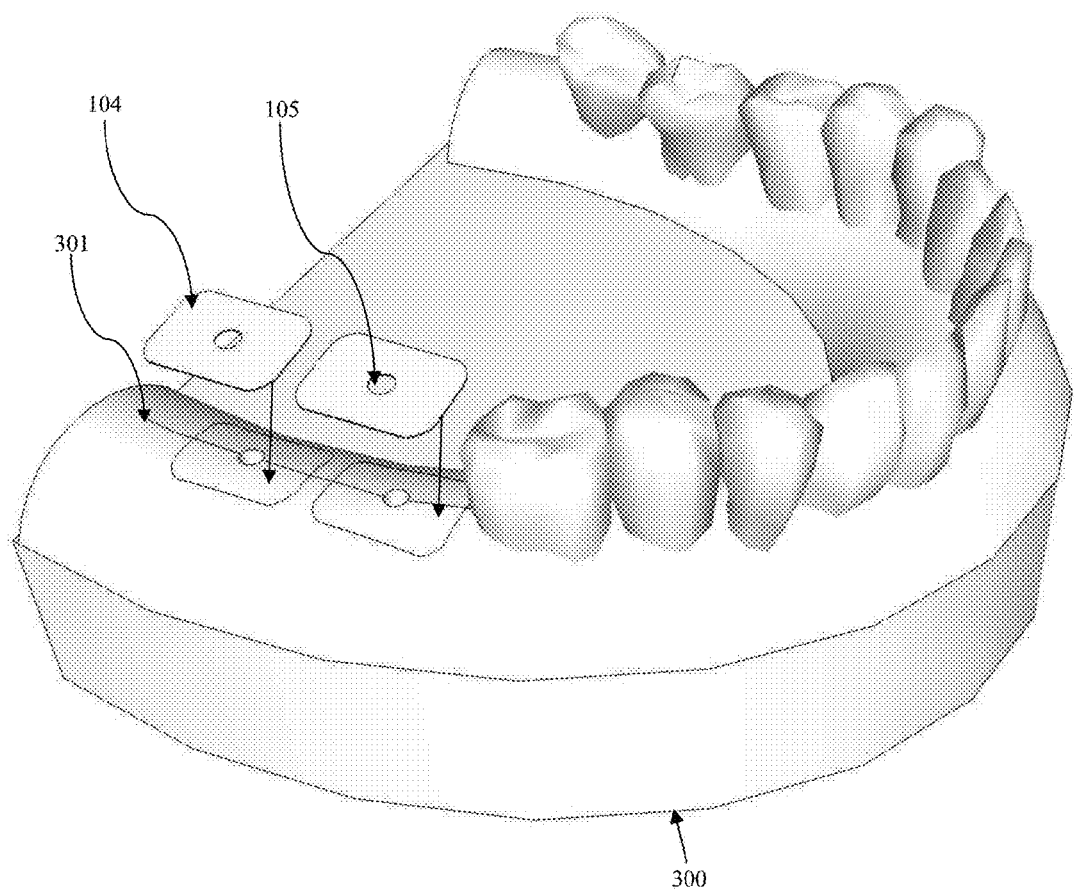
Figure 4:
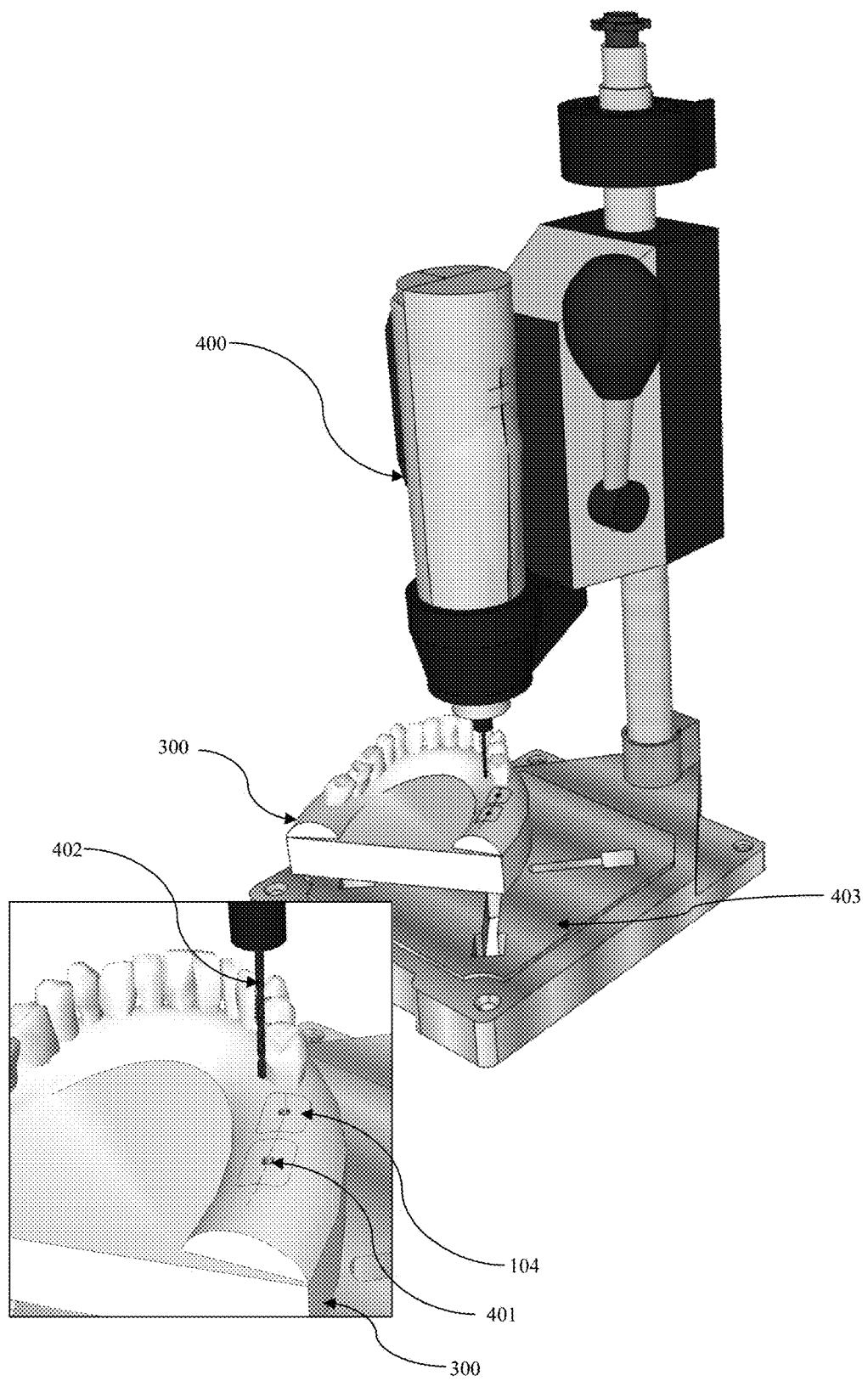
Figure 5:
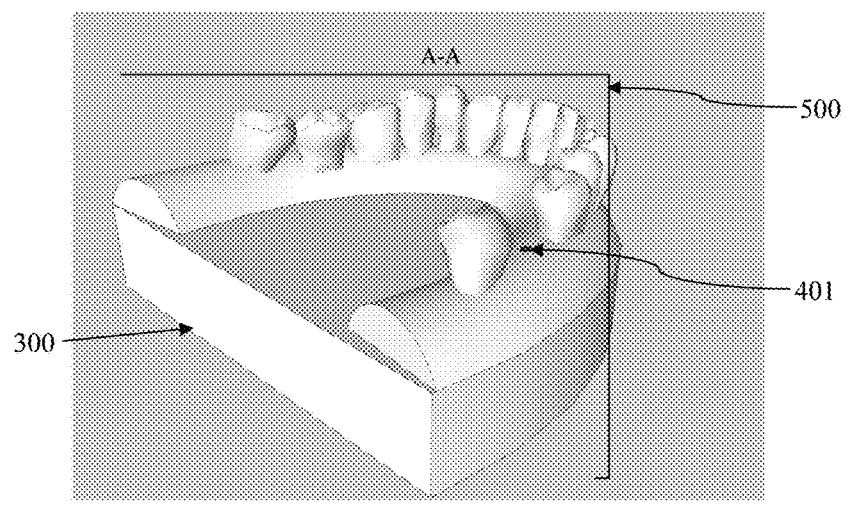
Figure 6:
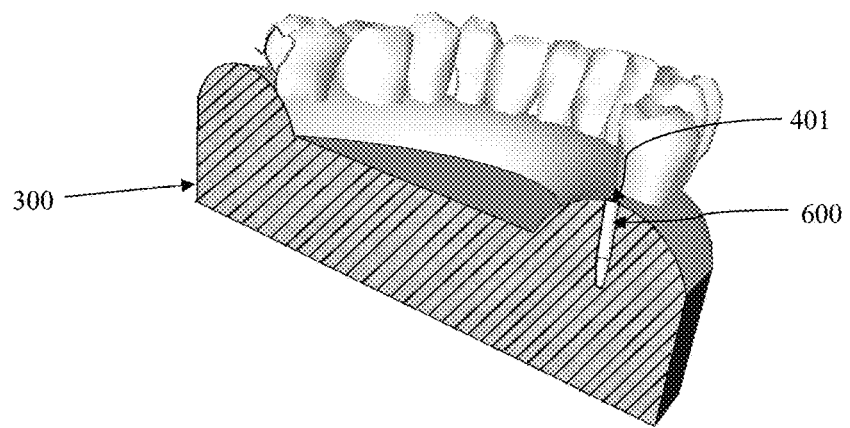
Figure 7:
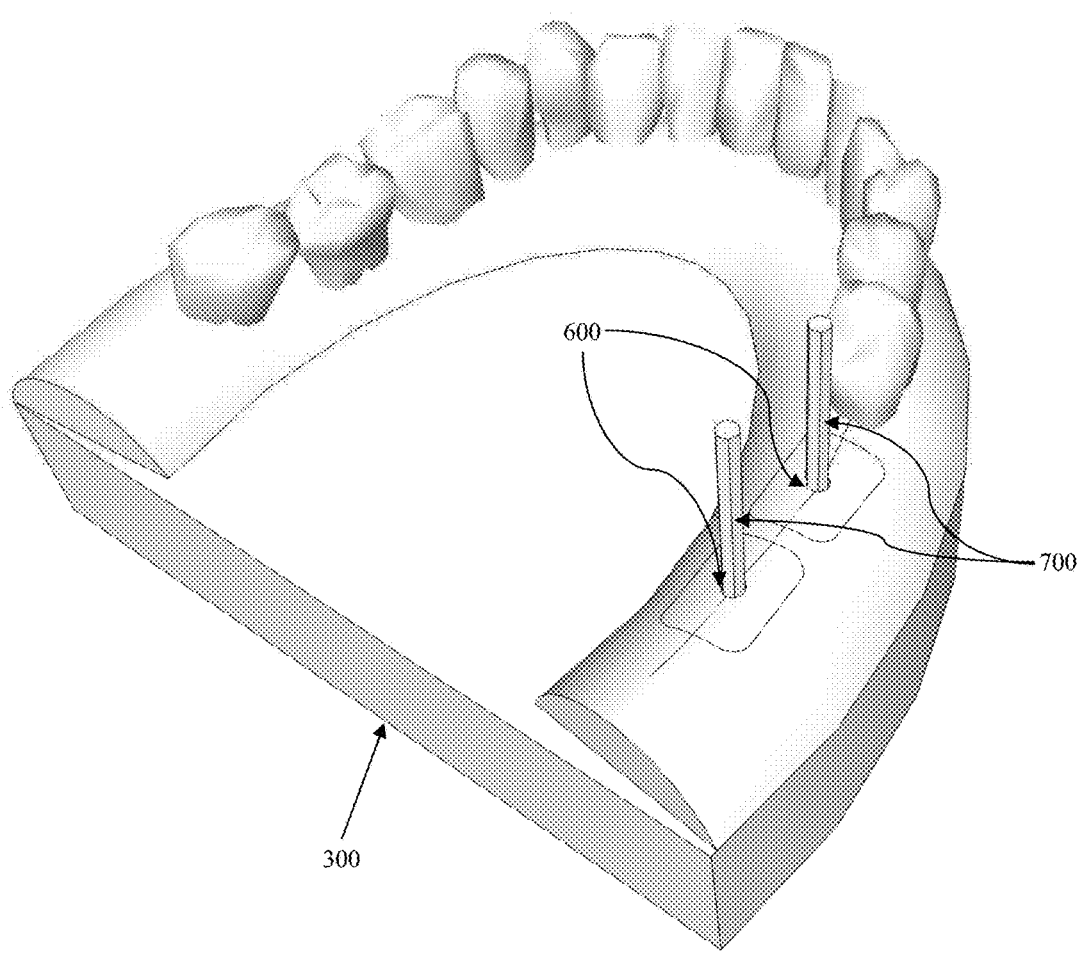
Figure 8:
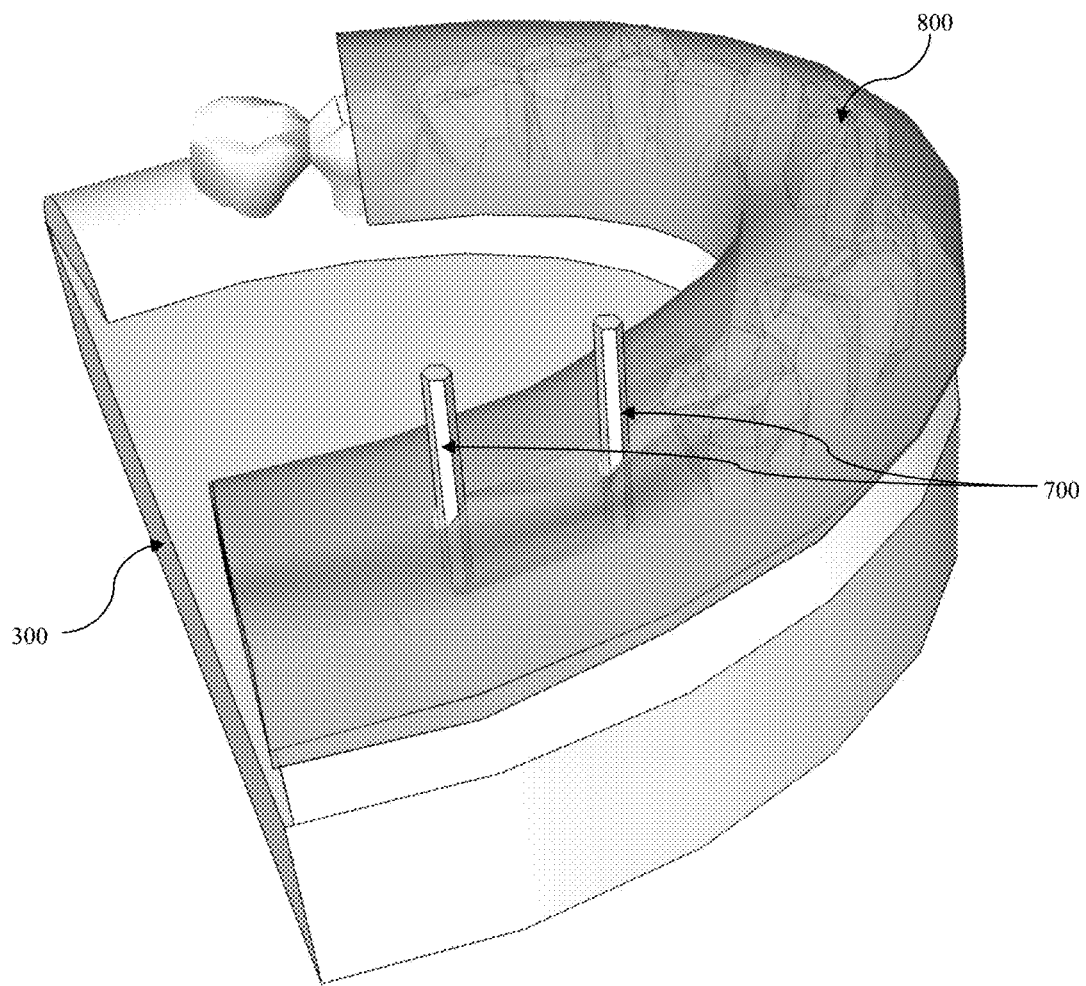
Figure 9:
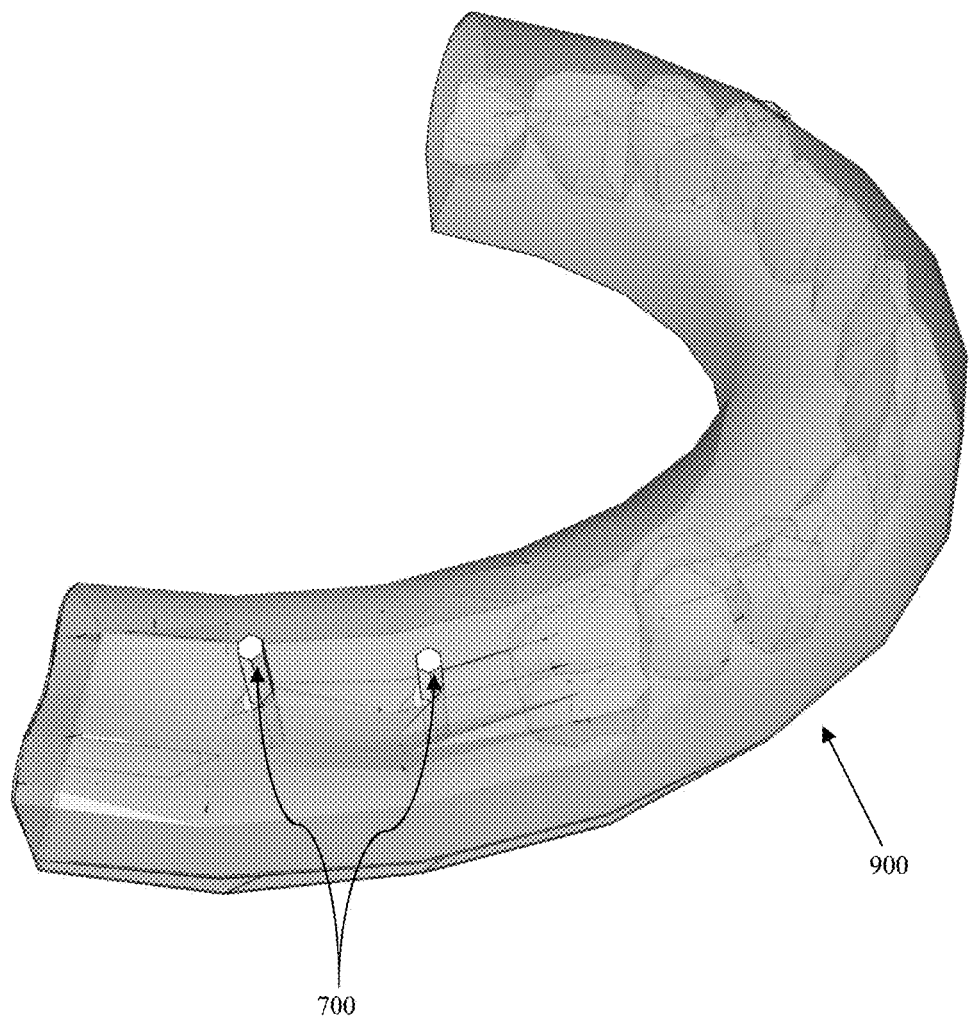
Figure 10:
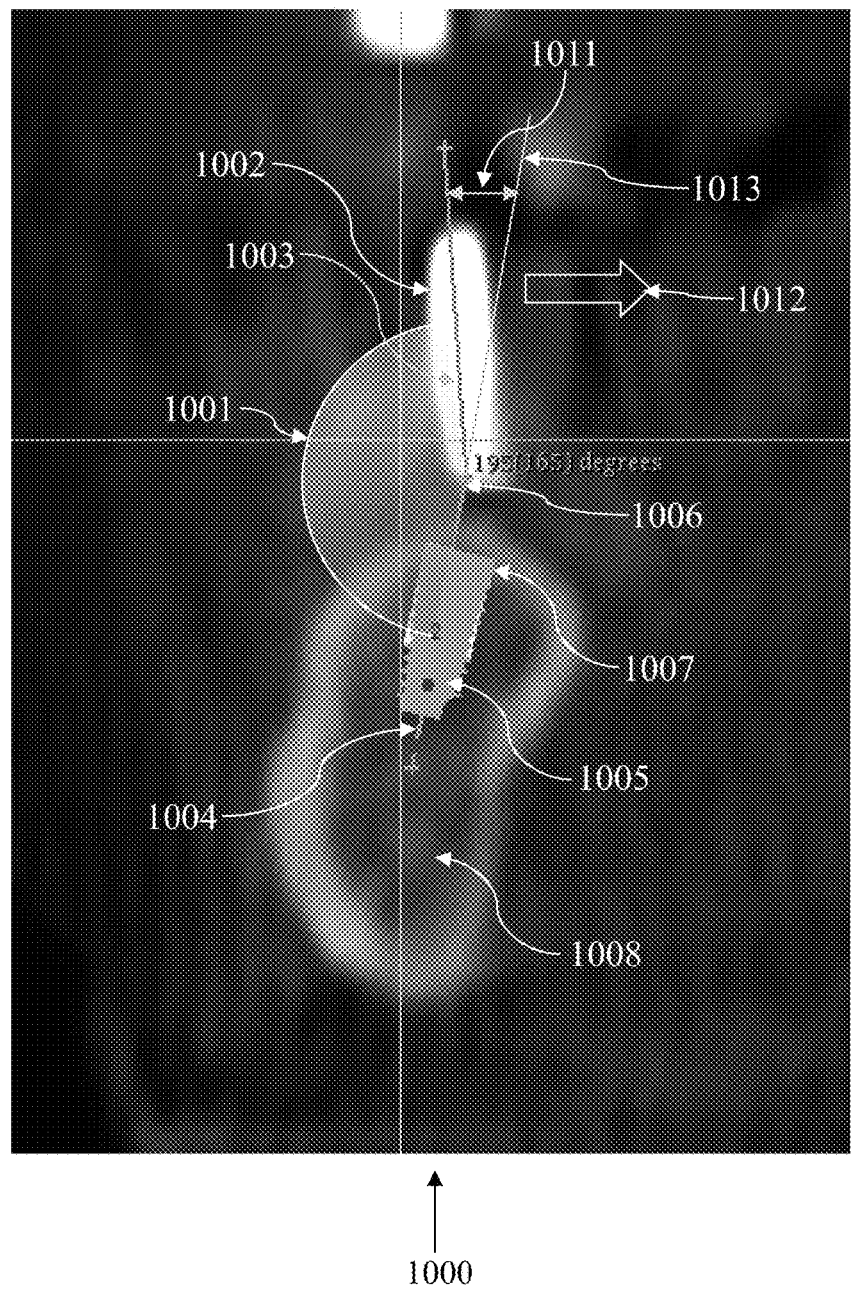
Figure 11:
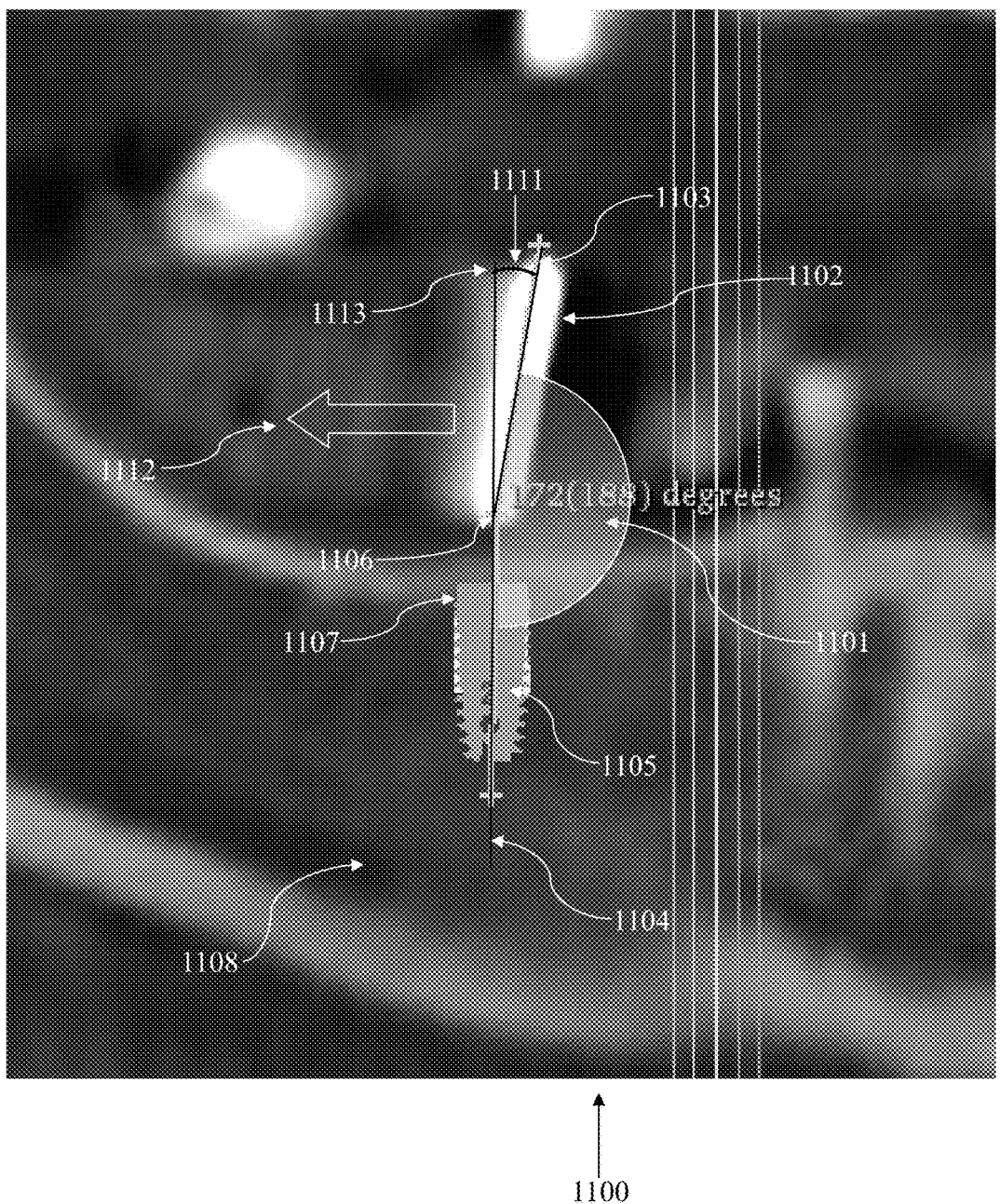
Figure 12:
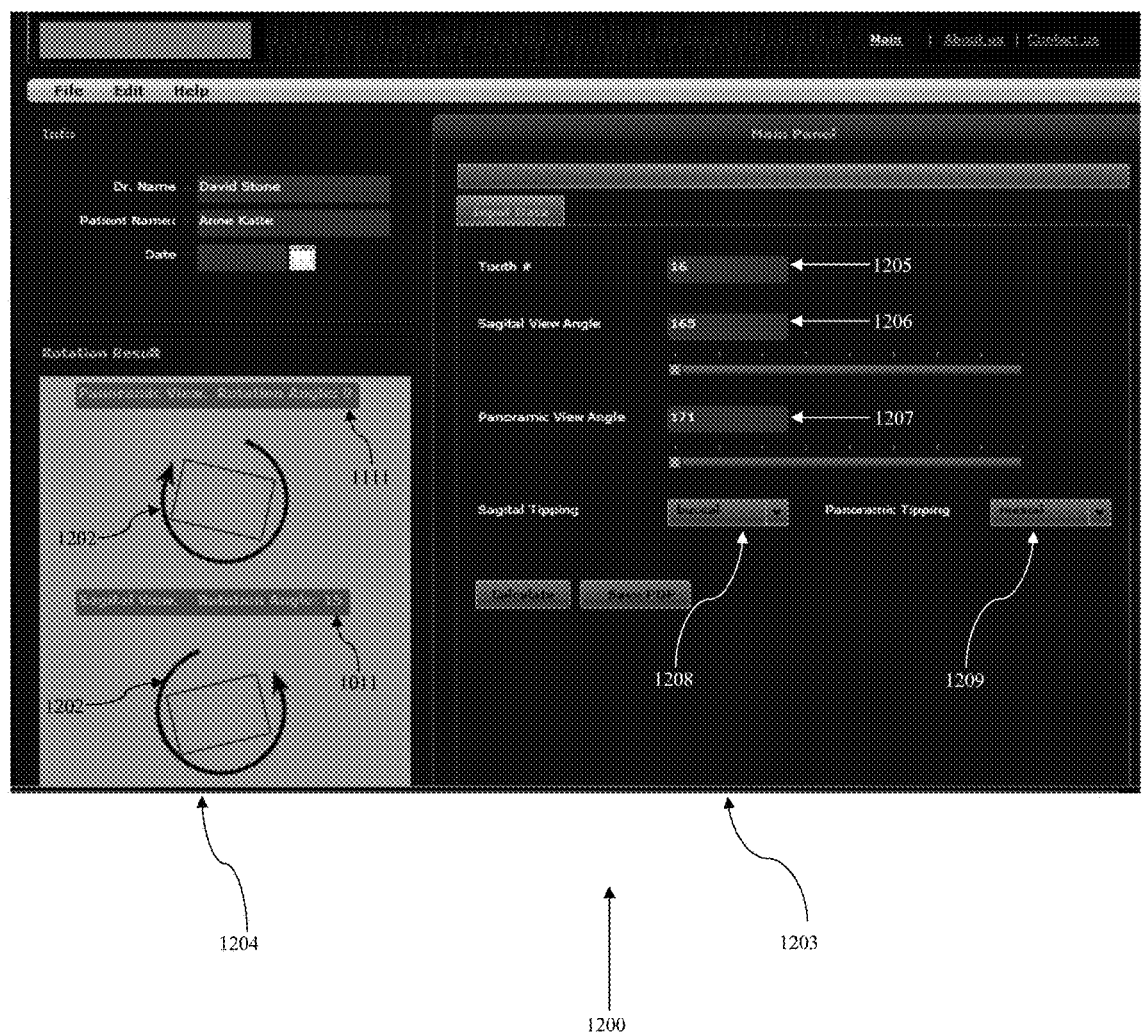
Figure 13:
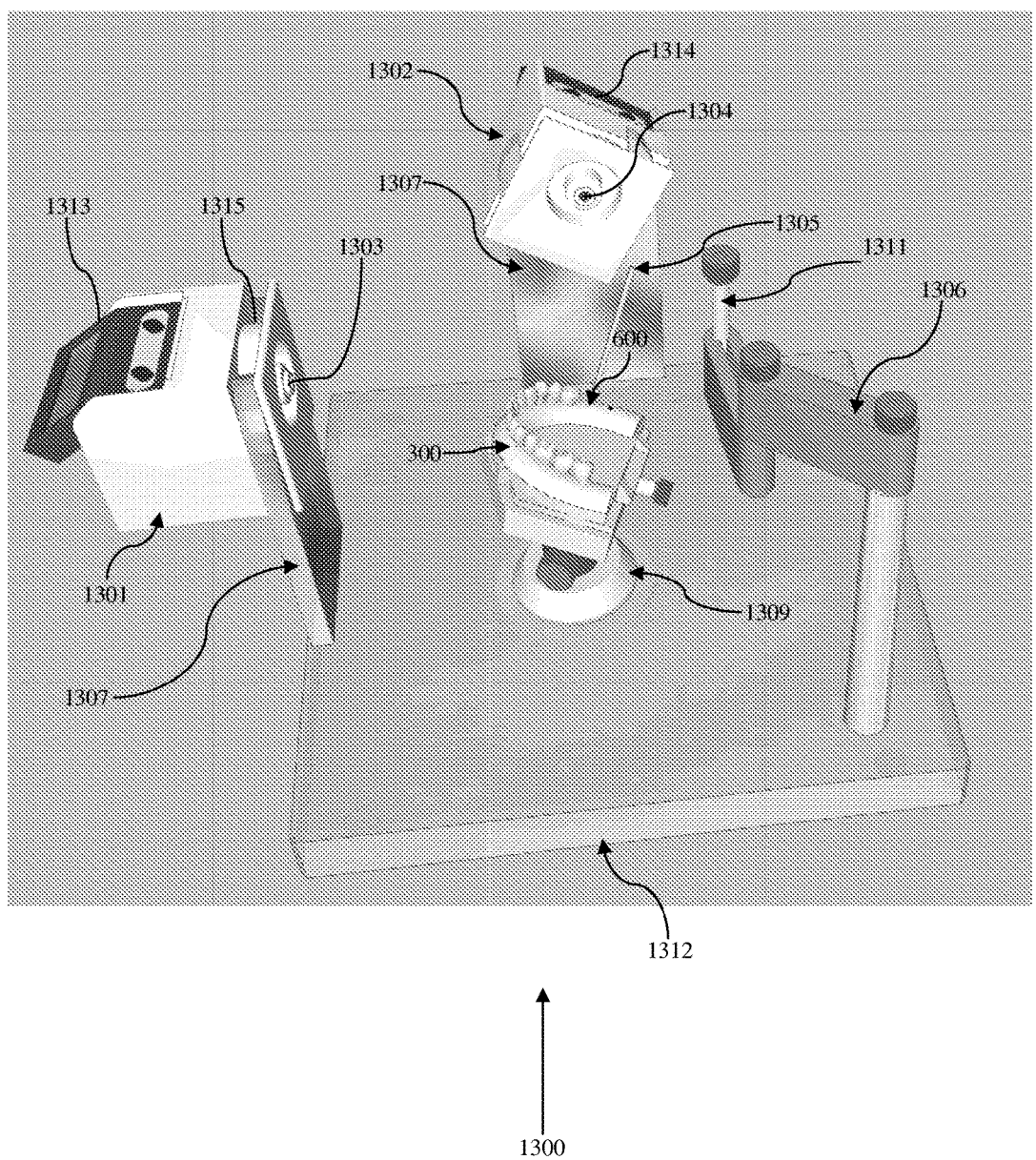
Figure 14:
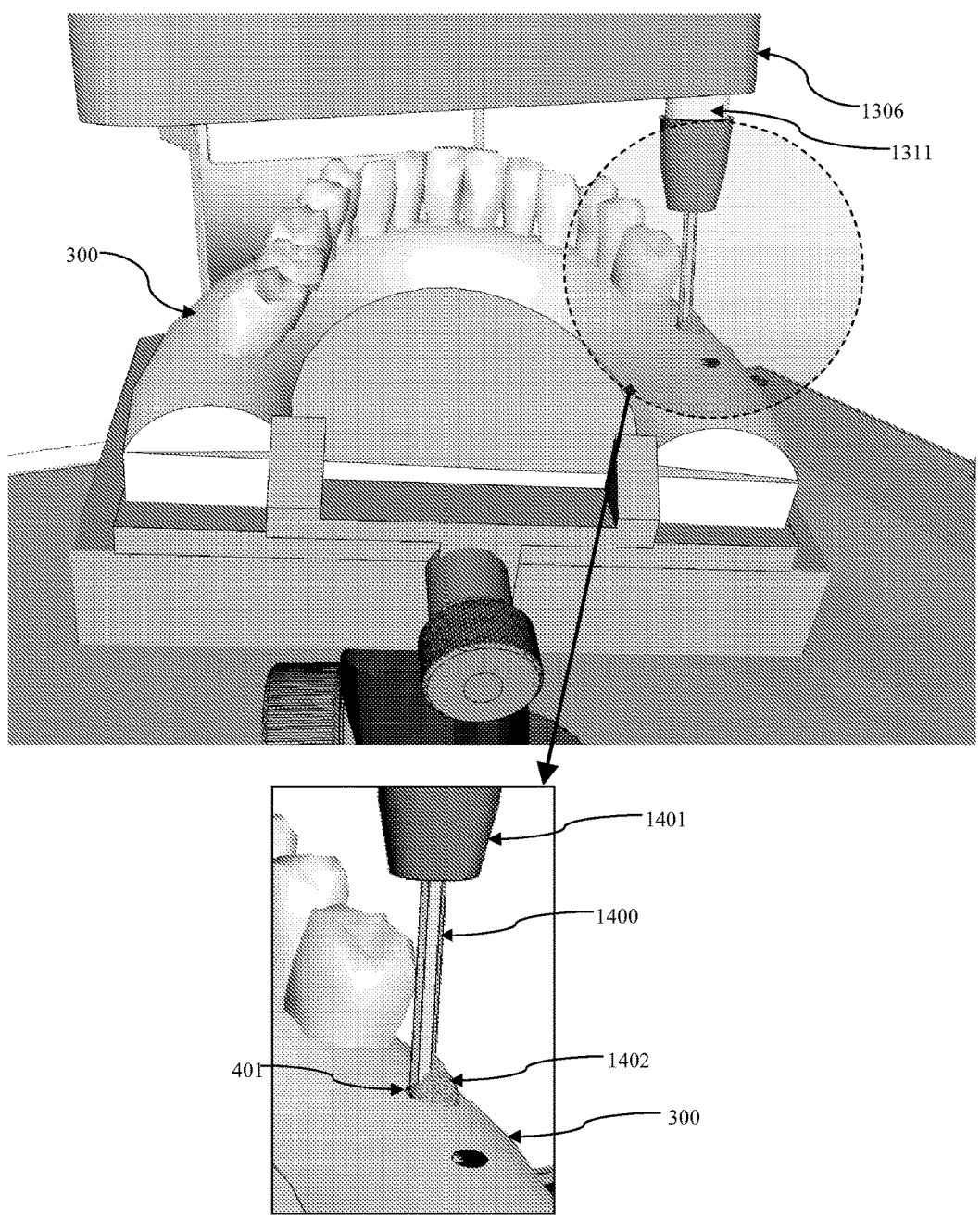
Figure 15:
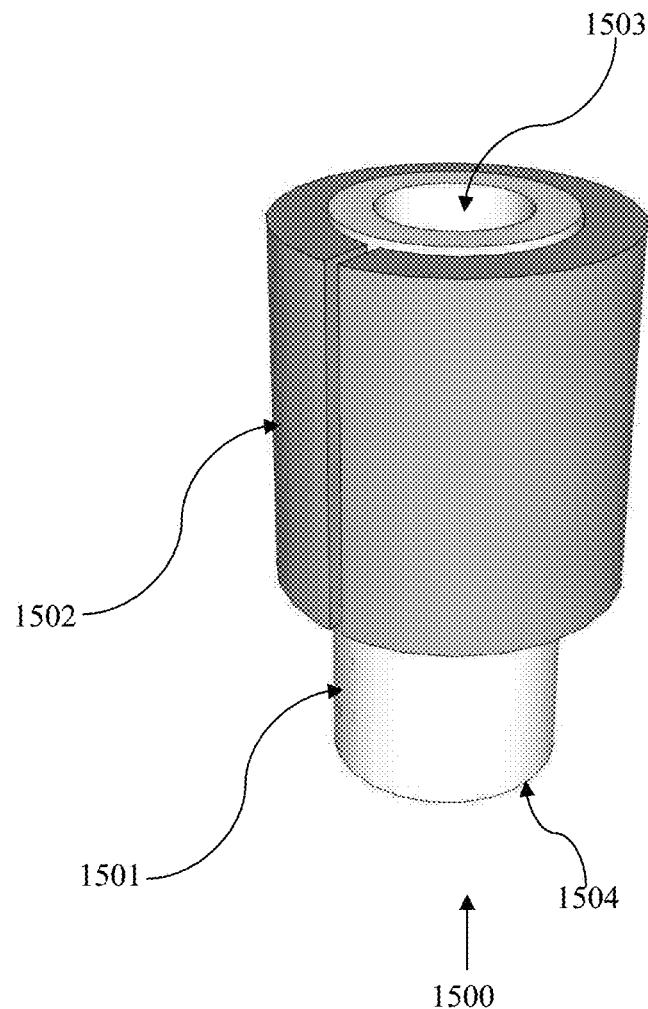
Figure 16:
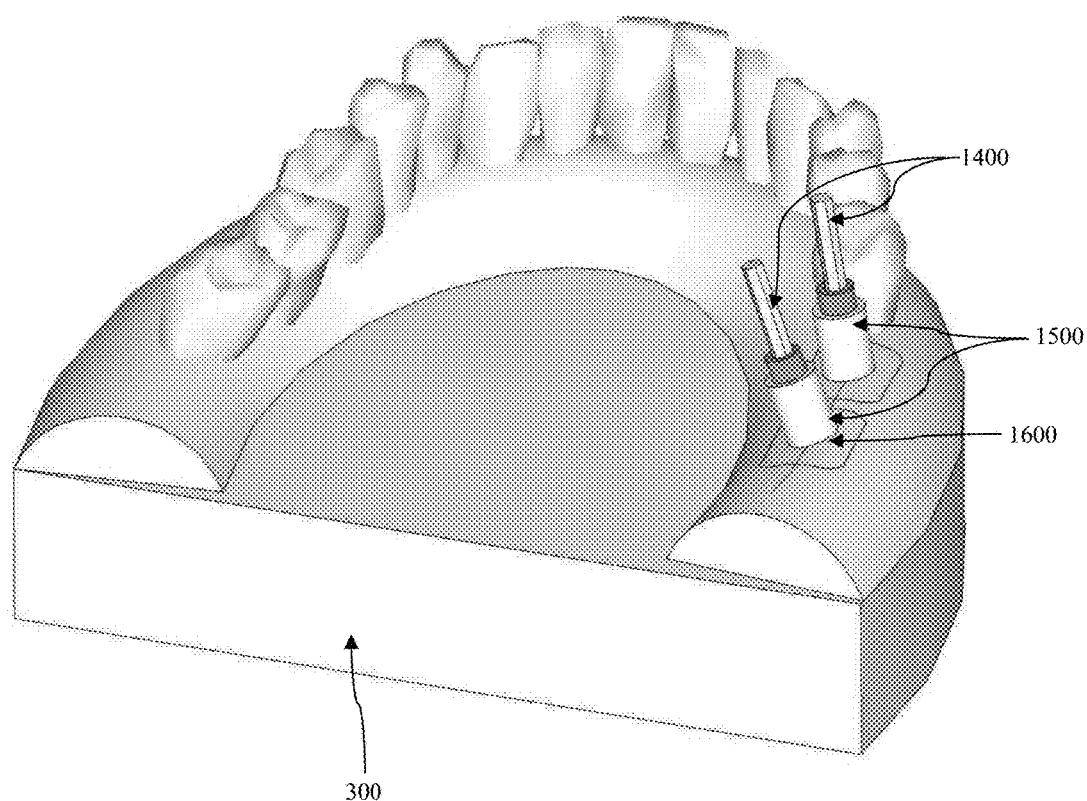
Figure 17:
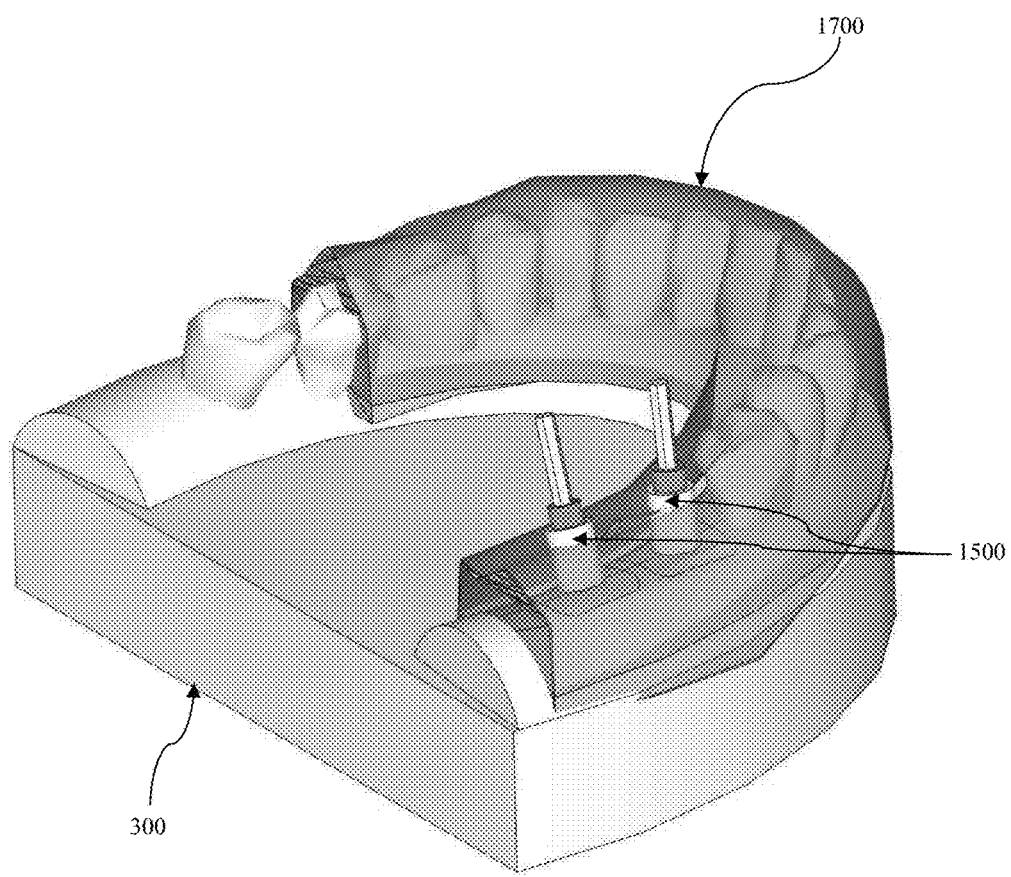
Figure 18:
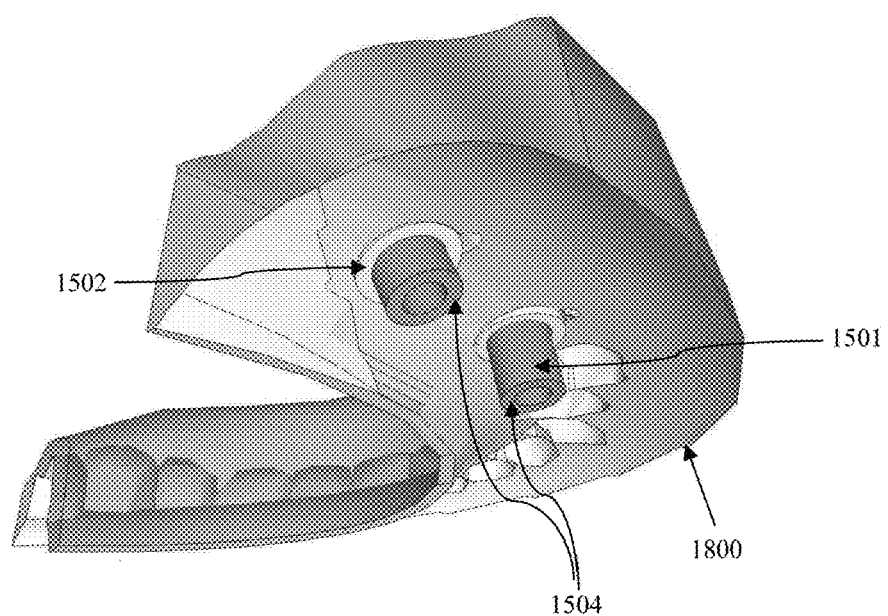
Figure 19:
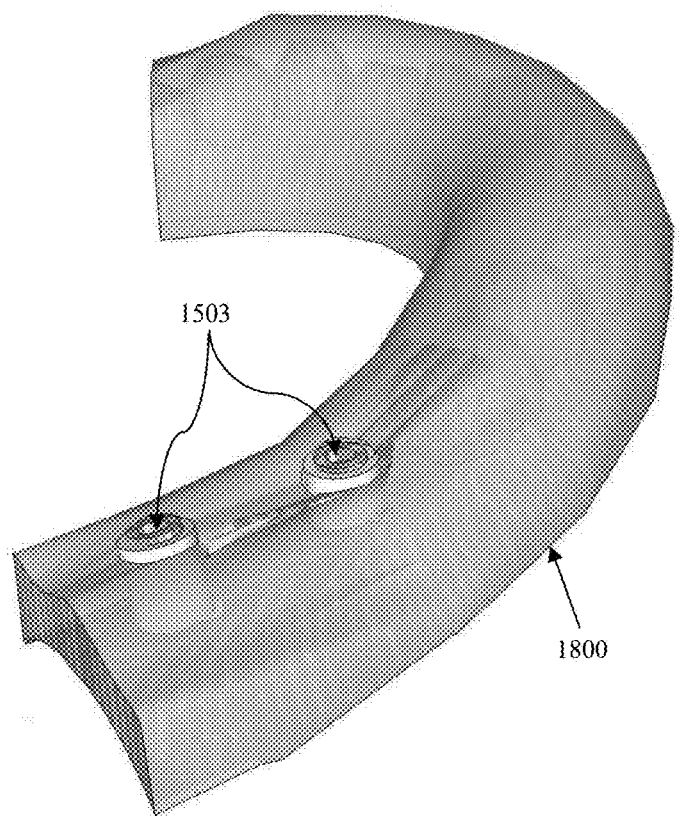
Figure 20:
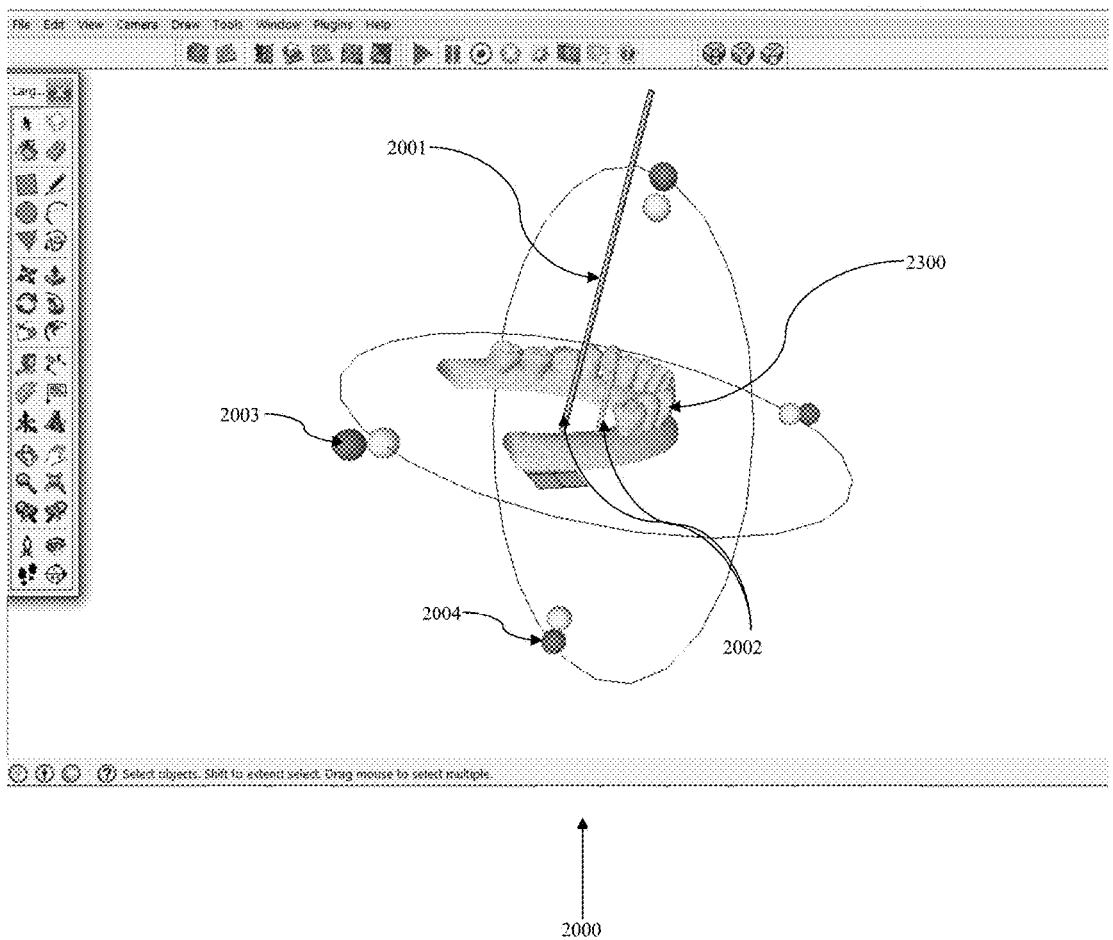
Figure 21:
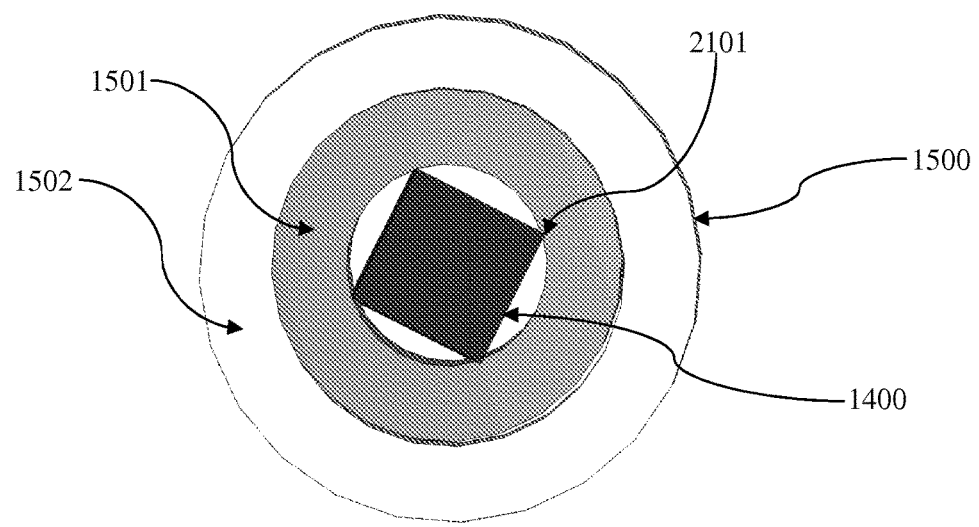
FIG. 21 shows a top view of the telescopic composed drilling tube 1500 with inserted into it the radiopaque rod 1400, which is a disposable plastic stick with a polygonal cross-section. The radiopaque rod has vertexes 2101 which fits tightly the internal surface of the inner tube 1501.
Figure 22:
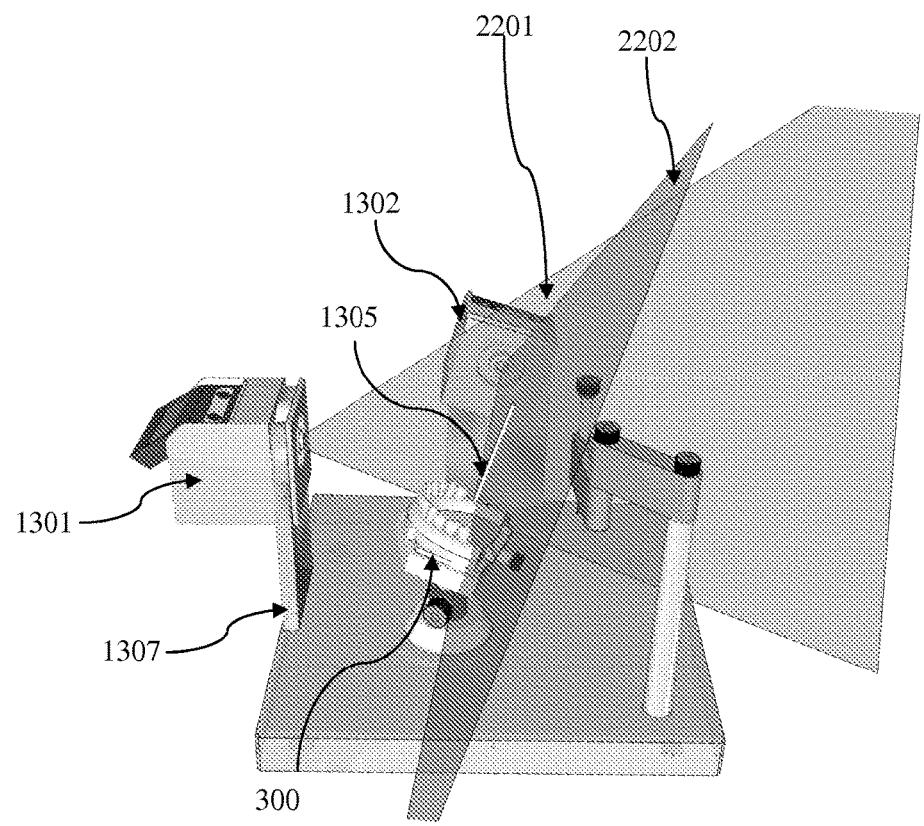

FIG. 22 shows the projection of the sagittal linear laser beam 2201 from the sagittal rotating head 1301. Also shown is the projection of the panoramic linear laser beam 2202 from the panoramic rotating head 1302. Shows the laser beam 2201 and the laser beam 2202 intersect on the removable linear reflector rod 1305 inserted into the straight cavity 600 into the cast model 300 when the dental cast model 300 is aligned in the direction of the osteotomy.

Figure 23:
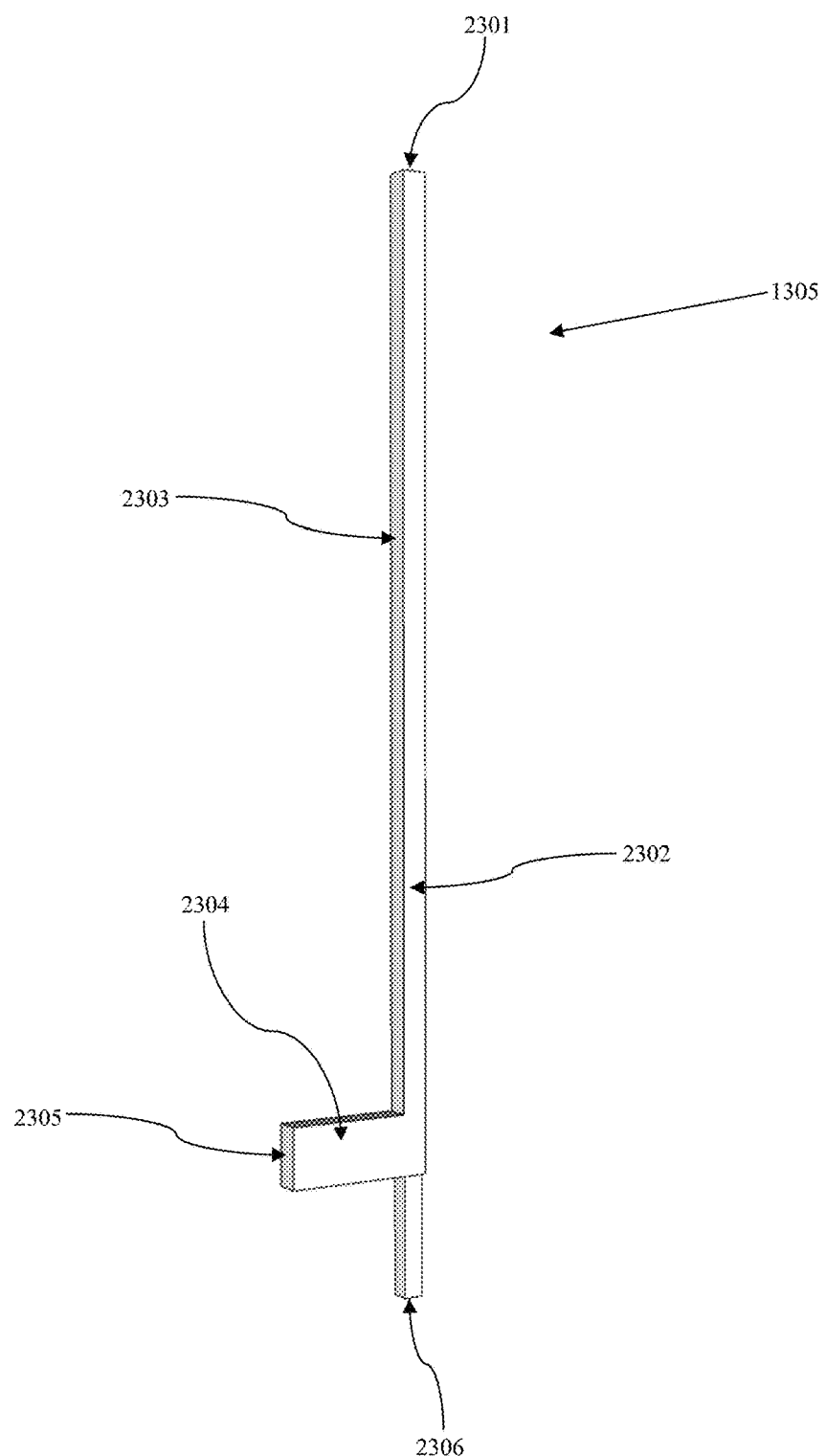

FIG. 23 shows the removable linear reflector rod 1305 with all its parts wherein 2301 is the body in shape of a long narrow rectangular cuboid rod, 2306 is the anchor in shape of a short narrow polygon cross-section rod, and 2304 is the horizontal extension in shape of rectangular cuboid extended from one side of the body 2301 right above the anchor 2306.

Figure 24:
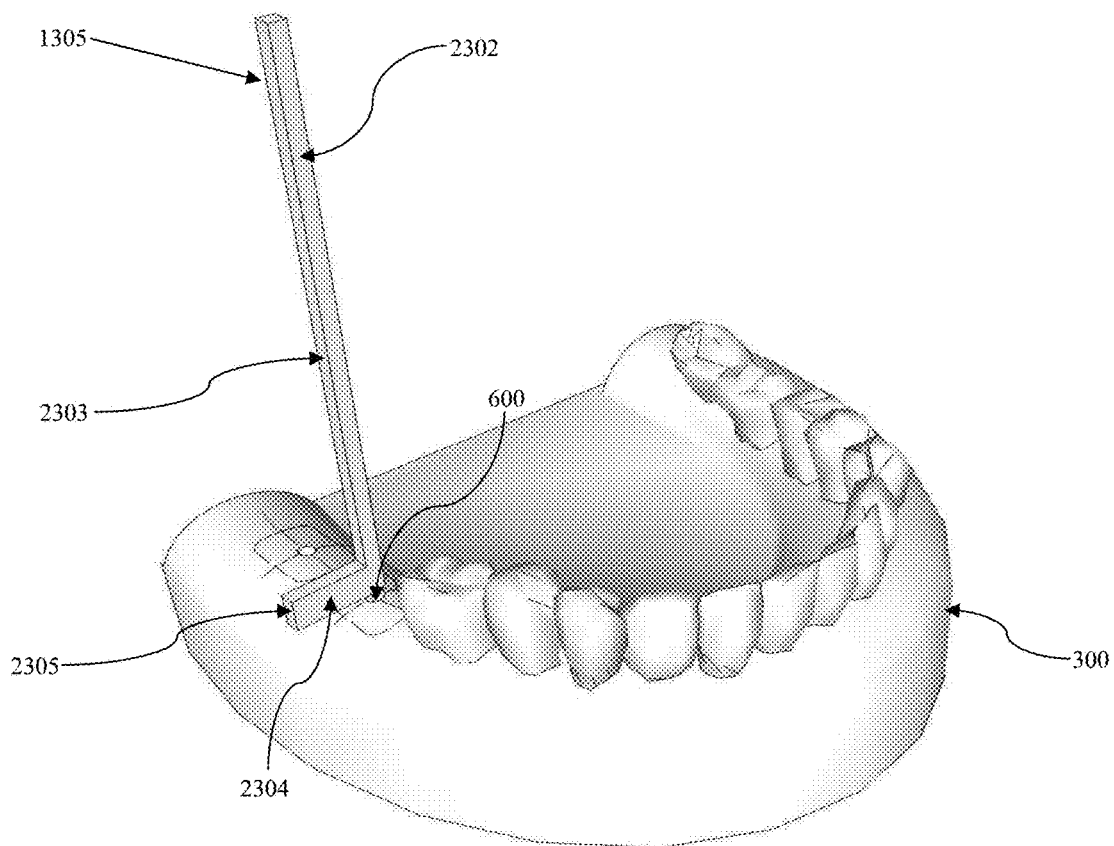

FIG. 24 shows the removable linear reflector rod 1305 inserted into the drilled cavity 600 of the dental cast model 300 prior the alignment procedure.

Figure 25:
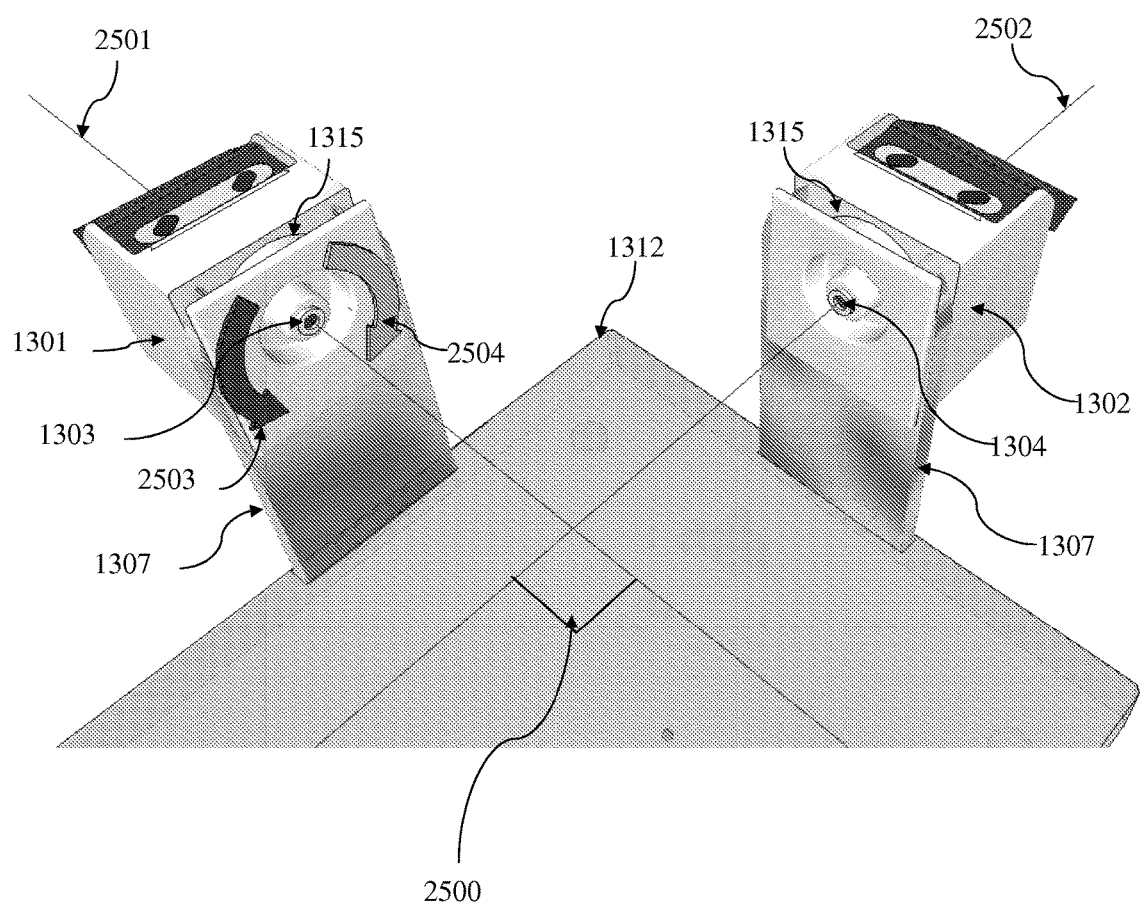

FIG. 25 shows the dental laser model aligner 1300 in isometric view where two vertical columns 1307 are attached to the horizontal platform 1312, each column has one rotating head 1301 or 1302. Each rotating head has an axis 2501 or 2502 of a rotation. Each axis 2501 or 2502 is parallel to the platform 1312 and these two axes intersect and form a right angle 2500. Each column has one rotating head 1301 or 1302 that comprises a bearing mechanism 1315 and a linear laser source 1303 or 1304 which is located on the axis of the rotation 2501 or 2502 of the rotating heads 1301 or 1302. The arrows 2503 and 2504 indicate the sense of rotation around the axis 2501 or 2502 of the rotating head clockwise or counter clockwise.

Figure 26:
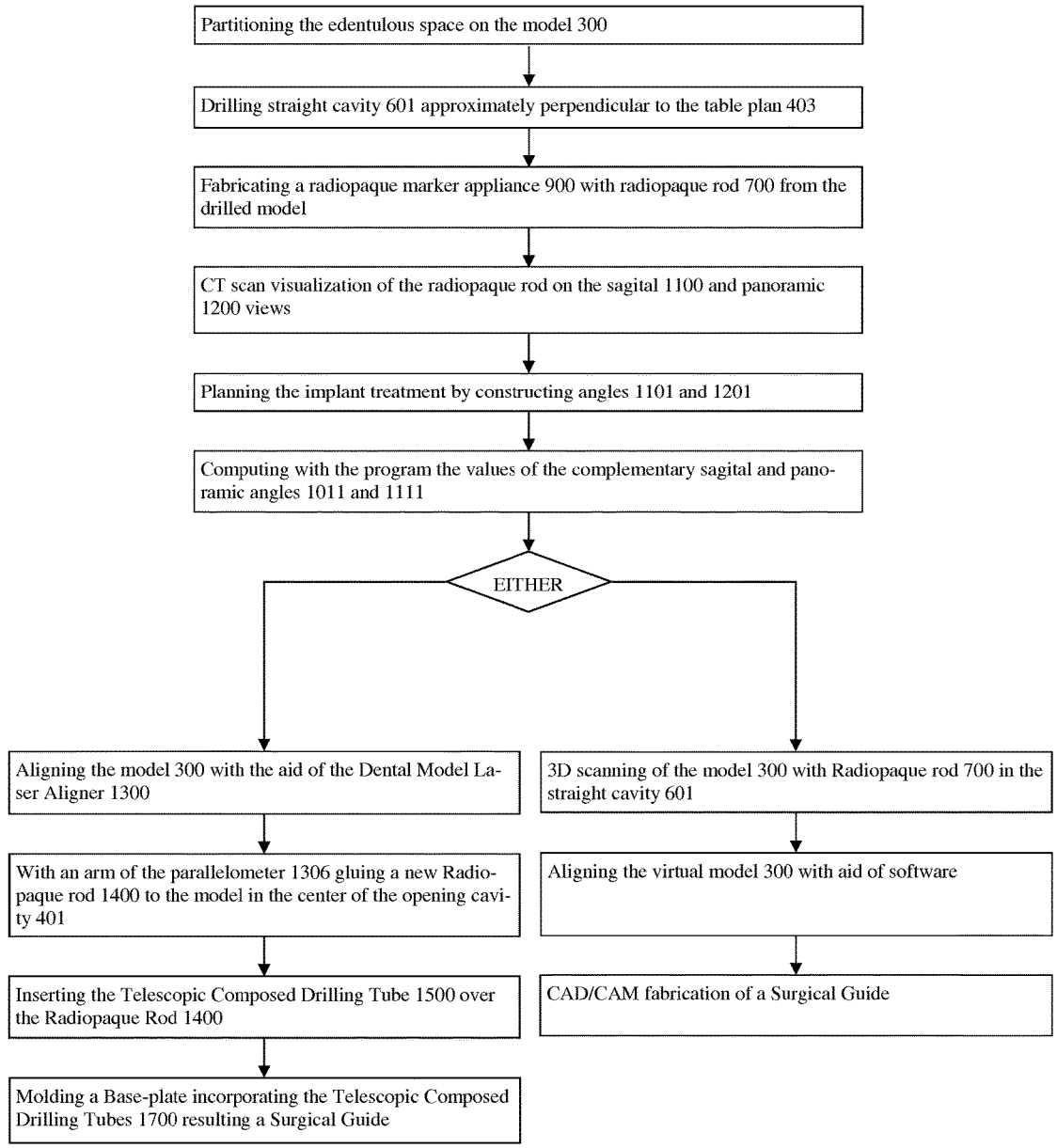

FIG. 26 is a step-by-step workflow diagram for the fabrication of a surgical guide, and it comprises of the steps of the present invention.

What I claim is:

1. A method for aligning a direction of a drilled cavity (600) of a dental cast model (300) with a direction of a planned dental osteotomy, the dental cast model (300) usable for making a surgical guide (1800) for the planned dental osteotomy, the method comprising:

inserting a radiopaque rod (700) in the drilled cavity (600) of the dental cast model (300);

molding a base plate (800) onto the dental cast model (300) for incorporating the radiopaque rod (700) and resulting in a radiopaque marker appliance (900);

removing the radiopaque marker appliance (900) that incorporates the radiopaque rod (700) from the dental cast model (300);

scanning the radiopaque marker appliance (900) using computed tomography or cone beam computed tomography of the radiopaque marker appliance (900) in a patient's mouth to produce a computed tomography image (2300) with radiopaque linear markers depicted thereon (1102, 1002);

constructing a sagittal angle (1001) between a long axis of a planned dental implant and a long axis of the radiopaque linear markers on a sagittal view (1000) of the computed tomography image (2300);

constructing a panoramic angle (1101) between the long axis of the planned dental implant and the long axis of the radiopaque linear markers on a panoramic view (1100) of the computed tomography image (2300);

calculating with a computer program (1200) the value of a first angle, a sagittal complementary angle (1011) of the sagittal view (1000) and the value of a second angle, a panoramic complementary angle (1111) of the panoramic view (1100) based on the sagittal angle (1001) and the panoramic angle (1101);

sliding and articulating an adjustable holder (1309) mounted onto a platform (1312) for holding the dental cast model (300), the adjustable holder (1309) being slidable and articulatable with respect to the platform (1312);

inserting a reflector rod (1305) that is removably insertable into the drilled cavity (800) of the cast model (300), the reflector rod (1305) including a rectangular cuboid rod member (2301) having a first longitudinal side with a first reflecting surface (2302) and a second longitudinal side with a second reflecting surface (2303), the first reflecting surface (2302) being perpendicular to the second reflecting surface (2303), the reflector rod (1305) including a horizontal extension in the shape of a rectangular cuboid member (2304) extending perpendicularly from the second longitudinal side and having a third reflecting surface (2305) that is parallel to the first reflecting surface (2302);

turning on a first linear laser source (1303) mountable on a first side of the platform (1312) for projecting a sagittal laser beam (2201);

adjusting a first protractor (1313) and a first rotating head (1301) associated to the first linear laser source (1303) for setting the first angle (1011) of the sagittal laser beam (2201);

turning on a second linear laser source (1304) on a second side of the platform (1312) that is perpendicular to the first side of the platform (1312) for projecting a panoramic laser beam (2202);

adjusting a second protractor (1314) and a second rotating head (1302) associated to the second linear laser source (1304) for setting the second angle (1111) of the panoramic laser beam (2202); and sliding and articulating the adjustable holder (1309) to align the sagittal laser beam (2201) on the first reflecting surface (2302) of the reflector rod (1305) and to align the panoramic laser beam (2202) on the second and third reflecting surfaces (2303, 2305) of the reflector rod (1305) whereby the drilled cavity (600) of the dental cast model (300) is aligned with the direction of the planned dental osteotomy.

* * * * *